(12) United States Patent
Sinn et al.

(10) Patent No.: US 6,177,561 B1
(45) Date of Patent: Jan. 23, 2001

(54) PREPARATION OF ACID AMIDES AND METALLIZATION OF COMPOUNDS

(75) Inventors: Hannsjörg Sinn, Wiesloch; Wolfgang Maier-Borst, Dossenheim; Hans-Hermann Schrenk, Zeiskam; Gerd Stehle, Wieblingen, all of (DE)

(73) Assignee: Deutsches Krebsforschungszentrum Stiftung des Offentlichen Rechts, Heidelberg (DE)

( * ) Notice: Under 35 U.S.C. 154(b), the term of this patent shall be extended for 0 days.

(21) Appl. No.: 09/367,768

(22) PCT Filed: Feb. 19, 1998

(86) PCT No.: PCT/DE98/00496

§ 371 Date: Dec. 6, 1999

§ 102(e) Date: Dec. 6, 1999

(87) PCT Pub. No.: WO98/37057

PCT Pub. Date: Aug. 27, 1998

(30) Foreign Application Priority Data

Feb. 19, 1997 (DE) ............................................. 197 06 490

(51) Int. Cl.[7] ........................ C07F 9/6524; C07C 231/02
(52) U.S. Cl. ........................... 540/145; 540/472; 540/474
(58) Field of Search ................................. 540/145, 472, 540/474

(56) References Cited

U.S. PATENT DOCUMENTS 4,826,673 * 5/1989 Dean et al. ............................. 424/9
5,837,866 * 11/1998 Magda ................................. 540/145

FOREIGN PATENT DOCUMENTS

| 775005 | 5/1957 | (CH) . | |
| 1054044 | 1/1967 | (DE) | C09B/57/00 |
| WO90/03804 | 4/1990 | (WO) . | |
| WO91/18630 | 12/1991 | (WO) . | |
| WO96/32134 | 10/1996 | (WO) . | |

* cited by examiner

Primary Examiner—John M. Ford
Assistant Examiner—Pavanaram K. Sripada
(74) Attorney, Agent, or Firm—Steven J. Hultquist; William A. Barrett

(57) ABSTRACT

The present invention relates to a process for preparing acid amides by reacting an acid with an aliphatic amine in molten urea. This invention also concerns a process for metalating compounds which can be bonded to a metal ion by reacting the compound with a metal ion in molten urea. Furthermore, the invention deals with the thus obtained products and their use for the therapy and/or diagnosis of tumors or inflammatory diseases.

28 Claims, 6 Drawing Sheets

PREPARATION OF ACID AMIDES AND METALLIZATION OF COMPOUNDS

The present invention relates to processes for preparing acid amides and the metalation of compounds which can be bonded to a metal or metal ion, the thus obtained products and their use for the therapy and/or diagnosis of tumors or inflammatory diseases.

It is known to use compounds which can be bonded to a metal ion, e.g. diethylenetriamine pentaacetic acid (DTPA), porphyrines, phthalocyanines and naphthalocyanines, for the therapy and/or diagnosis of tumors. In order to concentrate these compounds in a tumor and reduce the rate of elimination from a patient's body, polymolecular substances, e.g. polyethylene glycols, are bonded to these compounds. For bonding the polymolecular substances, the formation of acid amide bonds is made use of. However, the direct conversion of an acid with an amine fails. Therefore, the acid, e.g. $Gd^{3+}$-containing DTPA (Gd-DTPA) or tetrasulfophthalocyanine (TSPC) is first converted into an acid halide by using a halogenating agent. Excess halogenating agent is then separated. However, this often cannot be carried out fully or can only be done with great expenditure. The acid halide is then purified. Thereafter, it is reacted with an amine, e.g. amino-Ω-methoxy-polyethylene glycol (AMPEG) into an acid amide. Then, the acid amide must be purified. As a result, this process can be carried out only with great expenditure.

Metal ions can be bonded to the above compounds (DTPA, porphyrines, etc.). However, this often requires a long conversion period between the compounds and the metal ion. The product is also often obtained only in minor yield.

Thus, it is the object of the present invention to provide a process by which acid amides, optionally having a metal ion, can be produced simply, carefully and rapidly.

According to the invention this is achieved by the subject matters defined in the claims.

Therefore, the subject matter of the present invention relates to a process for preparing acid amides in which an acid is reacted with an amine in molten urea.

The expression "acid" comprises any kinds of acid, particularly carboxylic, sulfonic and phosphonic acids. The acid may also have several acid groups, e.g. 2 to 4. In the case of several acid groups they may be the same or differ. Preferred acids are diethylenetriamine pentaacetic acid (DTPA), diethylenetriamine pentamethylene phosphonic acid (DTPMPA), and acid group-containing porphyrine, such as tetrasulfophenyl porphyrine (TSPP) and tetracarboxyphenyl porphin (TCPP), an acid group-containing phthalocyanine such as tetrasulphophthalocyanine (TSPC), an acid group-containing naphthalocyanine, an acid group-containing chlorin, an acid group-containing bacteriochlorin, an acid group-containing chlorophyll, an acid group-containing bacteriochlorophyll or a derivative thereof.

The expression "porphyrine" comprises any kinds of compound having a macromolecular tetranuclear or polynuclear pyrrole backbone. Representatives of these compounds are porphyrines having one or several, preferably 4, functional acid groups. Further representatives are the expanded porphyrines such as saphyrine, rubyrine, pentaphyrine, superphthalocyanines or texaphyrines.

The expression "amine" comprises any kinds of compound having an aliphatic amino group. The amines may be primary or secondary amines. Examples of amines are tris, glucamine, glucosamine and aminopolyethers. The latter are polyethers, e.g. a polyethylene glycol, having an amino group, particularly a terminal amino group. The aminopolyether preferably has a molecular weight of 2,000 to 5,000 daltons.

A particularly preferred aminopolyether is amino-Ω-methoxy polyethylene glycol.

The acid is reacted with the amine in molten urea. In this connection, the molten urea functions as a solvent. The amount of urea can be chosen such that the educts and optionally also the products are dissolved in the molten urea. During the reaction, the amine is used in an excess, e.g. of 50%, particularly of 20%, based on the amount of acid groups to which the amine shall bond. The reaction temperature is 120 to 170° C., particularly preferably about 150 to 160° C. The reaction is concluded as soon as a substantially quantitative reaction has taken place. This can be determined easily by a person skilled in the art by common spectroscopic and/or chromatographic methods. The reaction time is usually 1 minute to 12 hours, particularly 10 to 20 minutes, most particularly about 15 minutes. Any containers used in chemistry and employable under these reaction conditions are suitable for the above process. It is particularly favorable to carry out the reaction in a closed vial. Heating can be effected e.g. in a steam autoclave.

The acid amide can be isolated by taking up the reaction batch in a solvent, optionally after cooling it down. Aqueous solvents such as water and acidic or alkaline buffers, such as 0.17 M $NaHCO_3$, where urea dissolves well, proved to be favorable solvents. The solvent can be chosen such that the products are dissolved therein. Then, the acid amide can be purified as usual, particularly by ultrafiltration. The acid amide can be dried, e.g. freeze-dried, or be dissolved in a solvent, such as water, dioxan, dimethylformamide (DMF), dimethyl acetamide (DMAA), dimethyl sulfoxide (DMSO) and dimethyl propyl urea (DMPH).

The subject matter of the present invention also relates to a process for metalating a compound which can be bonded to a metal ion and comprises the reaction of the compound with a metal ion in molten urea.

According to the invention the "compound which can be bonded to a metal ion" can be diethylenetriamine pentaacetic acid, diethylenetriamine pentamethylene phosphonic acid, a porphyrine, a phthalocyanine, a naphthalocyanine, a chlorin, a bacteriochlorin, a chlorophyll, a bacteriochlorophyll or a derivative thereof.

The compound which can bond a metal ion is preferably an acid (see above). The bond can be a complex bond or an ionic bond. The bond can be effected e.g. via 4 nitrogen atoms substantially arranged in one plane and connected to form a ring system, or via several, e.g. 3, of the above acid groups.

A metal ion can be bonded to such a compound. Examples of metal ions are ions of Al, Mg, Zn, Cu, Co, Fe, Ni, Pt, Pd, Gd, Ga and In. Examples of metal ions are particularly $Mg^{2+}$, $Cu^{2+}$, $Zn^{2+}$, $Ga^{3+}$, $Co^{3+}$, $Al^{3+}$, $Zn^{4+}$, $Pt^{4+}$, $Pd^{4+}$, and $Gd^{3+}$. The metal ion can be radioactive. It is favorable to chose the radii of the metal ions such that they fit into the compound structure in optimum fashion. If porphyrines, phthalocyanines, naphthalocyanines, chlorins, bacteriochlorins, chlorophyll or bacteriochlorophyll are used, the radius will favorably be less than 0.76 Å. If metal ions are used for the metalation, it will be favorable to add them as salts, e.g. hydroxides, to the reaction batch.

As described above, the acid can be a compound which can bond a metal ion. A metal ion can be bonded thereto. The metal ion bond can be effected during, before or after the reaction of the acid with the amine into acid amide, it being possible to effect the bond in molten urea. This can take place under substantially the same conditions as the acid amide formation in the molten urea.

Particularly preferred processes are shown in FIGS. 1 to 6.

The subject matter of the present invention distinguishes itself by a number of advantages. The process results in the products in a single reaction step without inserted purification steps. In this connection, the conversion is made quantitatively after a short time, particularly after about 15 minutes. Furthermore, no loss of metal or metal ion complexed with the acid can be observed. In this way, it is possible to produce in a direct reaction water-soluble macromolecular compounds of DTPA, porphyrine, phthalocyanine and naphthalocyanine complexes which are of significance for both tumor diagnosis and tumor therapy. These compounds were formerly not accessible at all or accessible only with great expenditure.

The below examples explain the invention:

EXAMPLE 1

Preparation of an Acid Amide From Gd-DTPA and Ampeg

Figure 1:
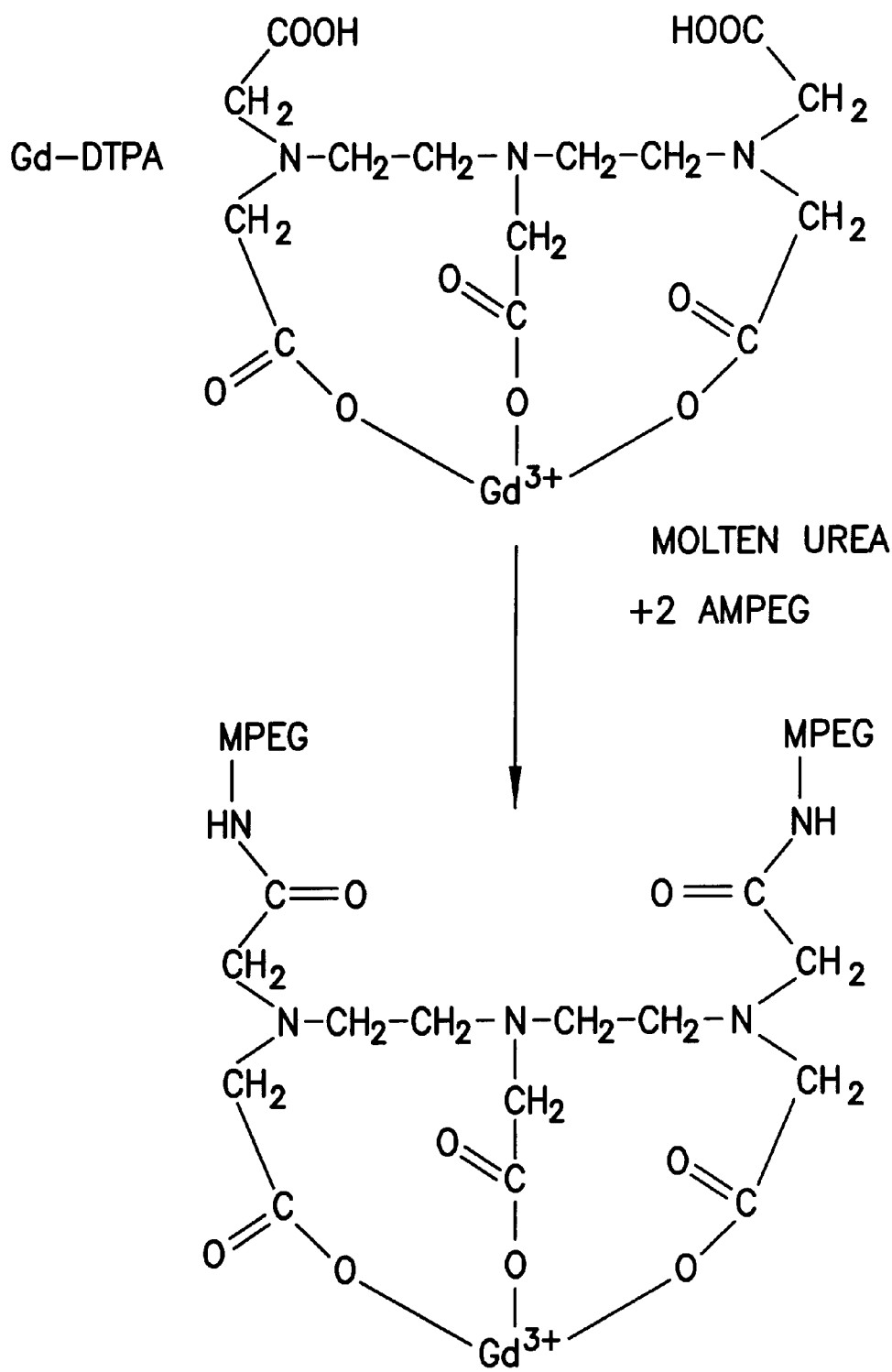
FIG. 1: shows the production of an acid amide from Gd-DTPA and AMPEG.

The preparation and the resulting acid amide are shown in FIG. 1.

50 mg of Gd-DTPA (0.09 mM) were charged together with about 3.5 g of urea and 1.2 g of AMPEG (0.24 mM/molecular weight ~5000) into a 15 ml vial having a bead closure, tightly sealed with a silicone rubber plug and an aluminum cap and heated in a steam autoclave to 155° C. for 15 minutes.

After cooling down to about 105° C., the autoclave was aerated, the reaction vessel was removed and the mostly solidified molten urea was dissolved in 10 ml of distilled water. The clear solution was transferred into an ultrafiltration cell for the purpose of purification and separation of undesired accompanying substances and washed 4 to 5 times on an ultrafilter (Amicon, YM5) (depletion factor >20×10⁵). An acid amide from Gd-DTPA and AMPEG was obtained. It can be lyophilized and be dissolved in water having any pH or in organic solvents (DMF, DMAA, DMSO, DMPH).

EXAMPLE 2

Preparation of an Acid Amide From Gd-DTPMPA and Ampeg

Figure 2:
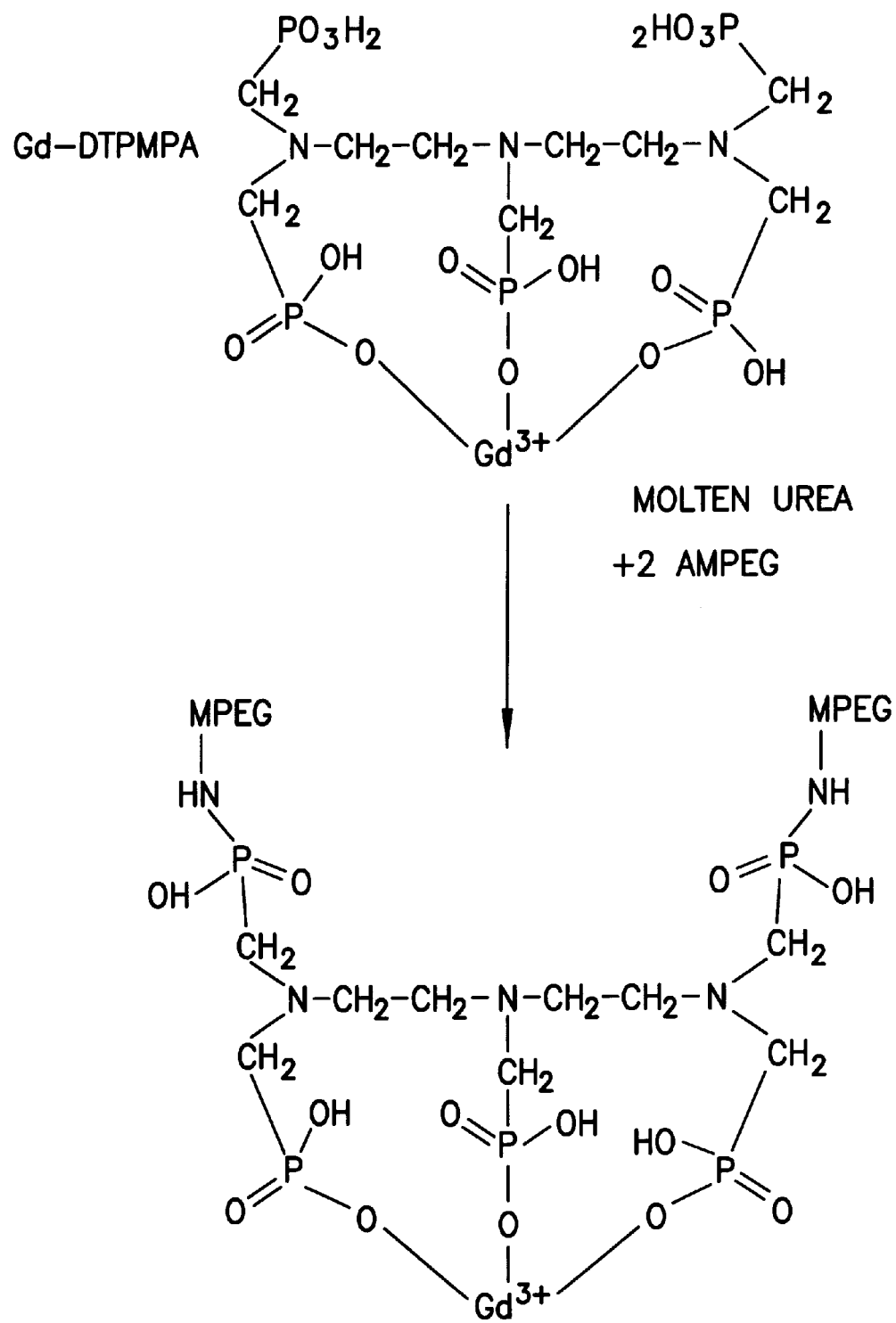
FIG. 2: shows the production of an acid amide from Gd-DTPMPA and AMPEG.

The preparation and the resulting acid amide are shown in FIG. 2.

The same process as in Example 1 was used with the exception that DTPMPA was employed in place of DTPA.

EXAMPLE 3

Preparation of an Acid Amide From TSPP and Ampeg

Figure 3:
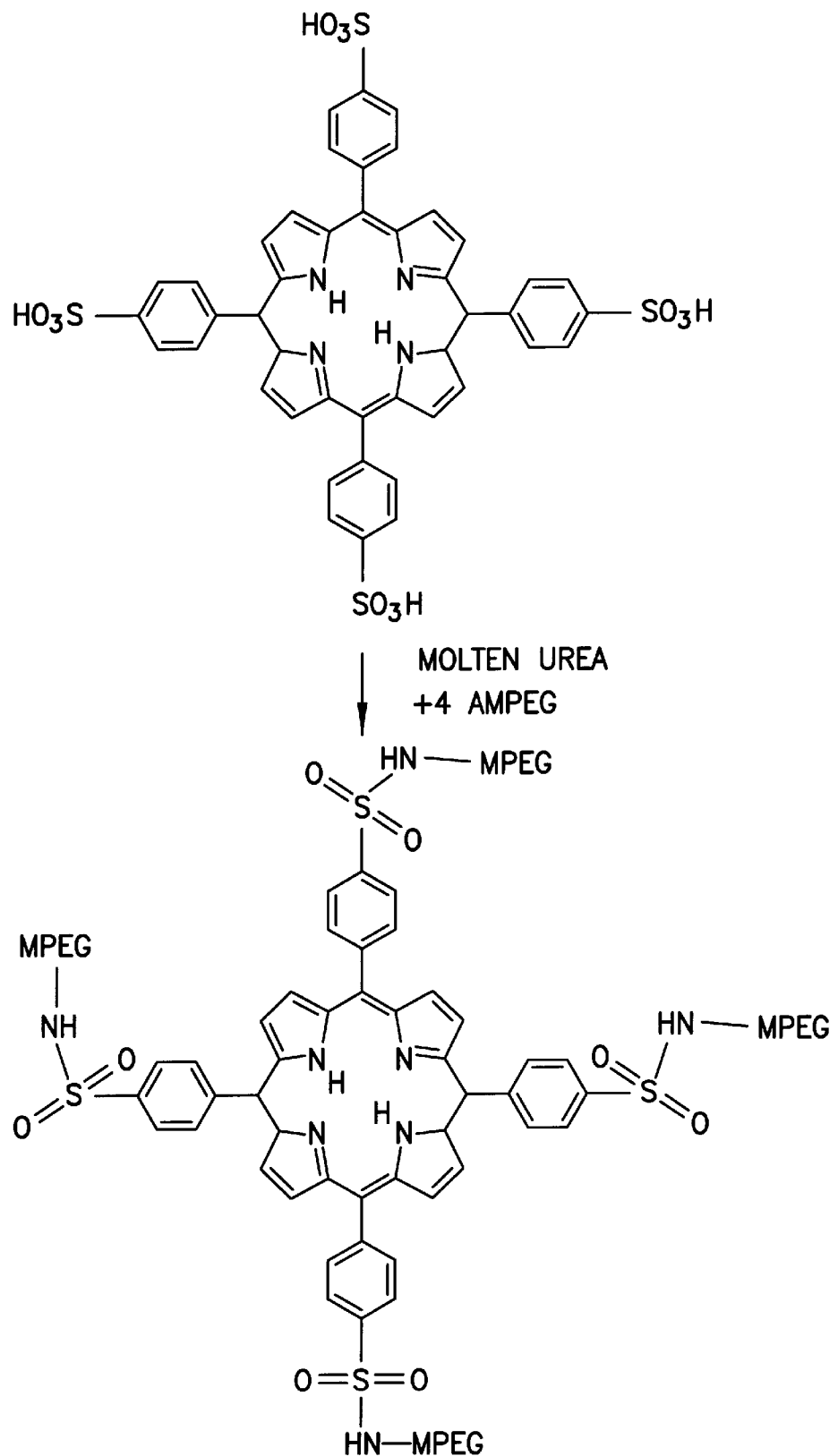
FIG. 3: shows the production of an acid amide from TSPP and AMPEG.

The preparation and the resulting acid amide are shown in FIG. 3.

About 40 mg of TSPP (tetra-(4-sulfophenyl)porphin, molecular weight ~934, Porphyrin Products) (0.043 mM) were charged together with about 3.5 g of urea and 1.2 g of AMPEG (0.24 mM) into a 15 ml vial having a bead closure, tightly sealed with a silicone rubber plug and an aluminum cap and heated in a steam autoclave to 155° C. for 1–5 minutes.

After cooling down to about 105° C., the autoclave was aerated, the reaction vessel was removed and the mostly solidified molten urea was dissolved in 10 ml of distilled water. The clear, deep-red solution was transferred into an ultrafiltration cell for the purpose of purification and separation of undesired accompanying substances and washed 4 to 5 times on an ultrafilter (Amicon, YM 10) (depletion factor >1×10⁵). An acid amide from TSPP and AMPEG was obtained. It can be lyophilized and be dissolved in water having any pH or in organic solvents (dioxan, DMF, DMAA, DMSO, DMPH).

EXAMPLE 4

Preparation of an Acid Amide From TSPC and Ampeg

Figure 4:
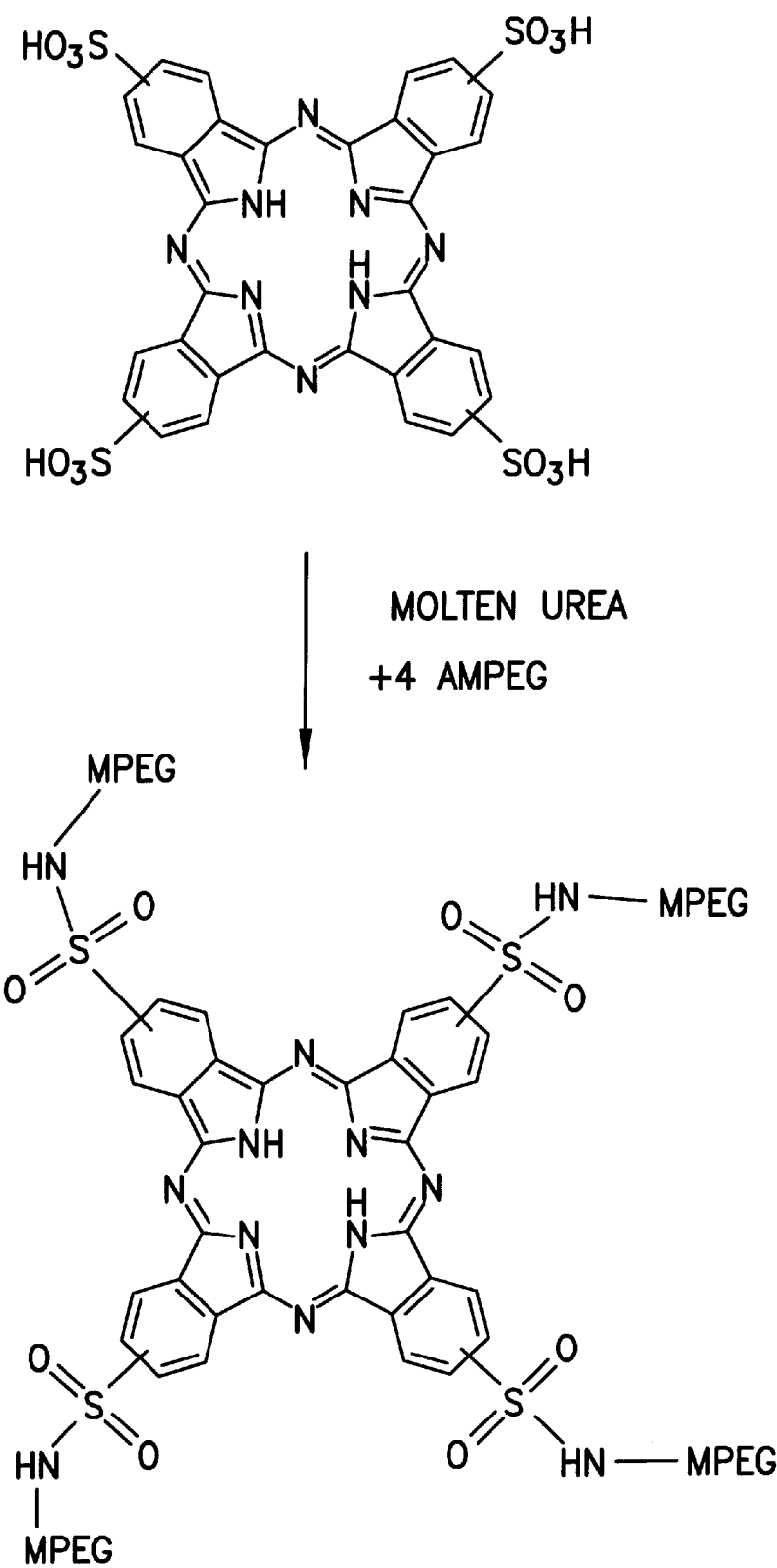
FIG. 4: shows the production of an acid amide from TSPC and AMPEG.

The preparation and the acid amide are shown in FIG. 4.

About 40 mg TSPC (tetra-sulfophthalocyanine, molecular weight ~836, Porphyrin Products) (0.048 mM) were charged together with about 3.5 g of urea and 1.2 g of AMPEG (0.24 mM) into a 15 ml vial having a bead closure, tightly sealed with a silicone rubber plug and an aluminum cap and heated in a steam autoclave to 155° C. for 15 minutes.

After cooling down to about 105° C., the autoclave was aerated, the reaction vessel was removed and the mostly solidified molten urea was dissolved in 10 ml of distilled water. The clear, deep-blue solution was transferred into an ultrafiltration cell for the purpose of purification and separation of undesired accompanying substances and washed 4 to 5 times on an ultrafilter (Amicon, YM 10) (depletion factor >2×10⁵). An acid amide from TSPC and AMPEG was obtained. It can be lyophilized and dissolved in water having any pH or in organic solvents (dioxan, DMF, DMAA, DMSO, DMPH).

EXAMPLE 5

Metalation of Tcpp with $Mg^{2+}$

Figure 5:
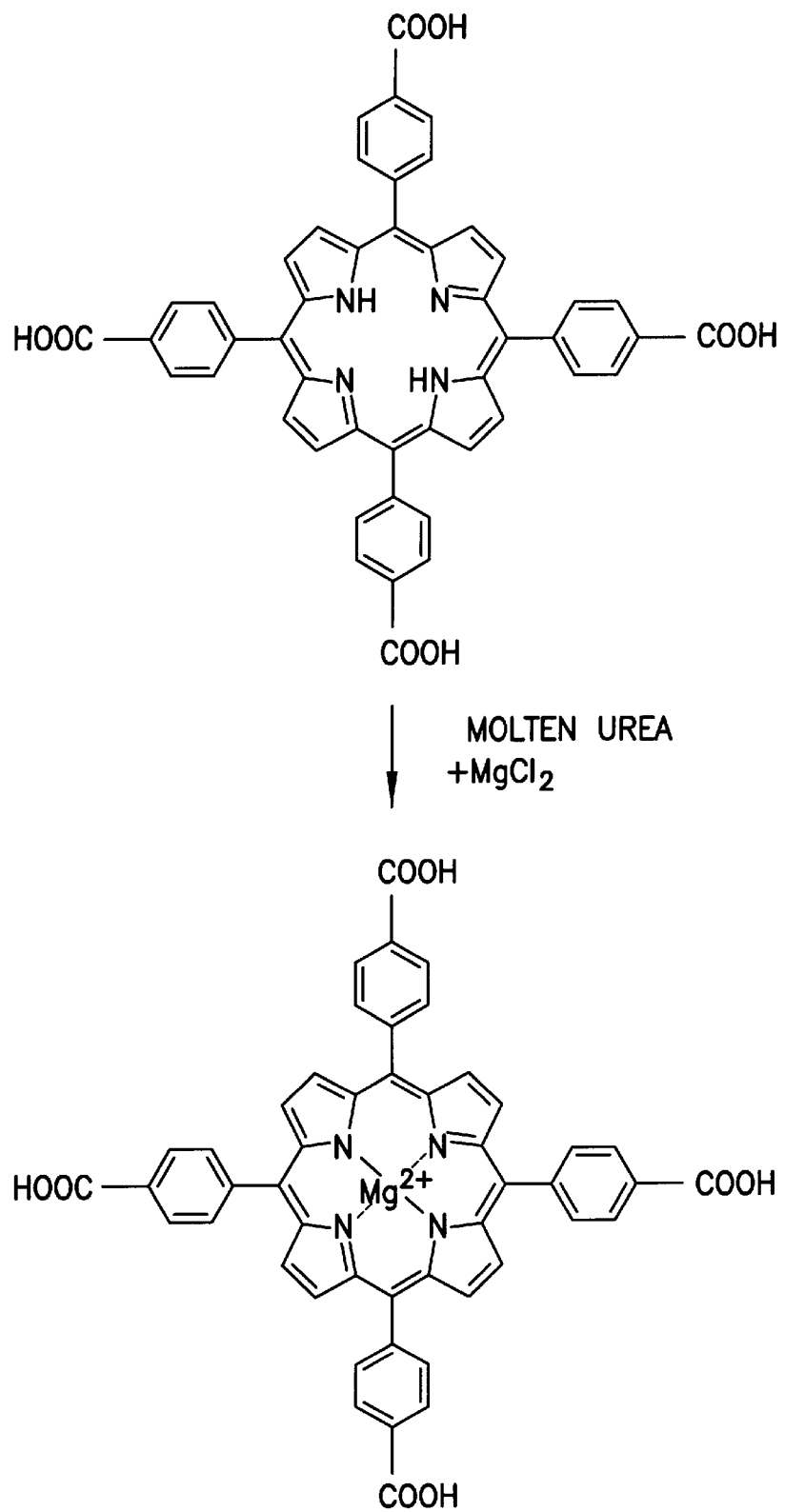
FIG. 5: shows the metalation of TCPP with $Mg^{2+}$.

The preparation and the resulting complex are shown in FIG. 5.

About 40 mg of TCPP (tetra-(4-carboxyphenyl)porphin, molecular weight=790) (0.05 mM) were charged together with about 3.5 g of urea and 70 mg of $Mg(OH)_2$ (1.2 mM) into a 15 ml vial having a bead closure, tightly sealed with a silicone rubber plug and an aluminum cap and heated in a steam autoclave to 155° C. for 15 minutes.

After cooling down to about 105° C., the autoclave was aerated, the reaction vessel was removed and the mostly solidified molten urea was dissolved in 10 ml of 0.17 M $NaHCO_3$. The clear, dichroic solution was transferred into an ultrafiltration cell for the purpose of purification and separation of undesired accompanying substances and washed 4 to 5 times on an ultrafilter (Amicon, YC 05) (depletion factor >2×10⁵). A complex from TCPP and $Mg^{2+}$ was obtained. It can be isolated by freeze-drying and then be reacted with amines such as tris, glucamine, glucosamine, MPEG, etc., in molten urea to give an acid amide.

EXAMPLE 6

Simultaneous Metalation and Acid Amide Formation

Figure 6:
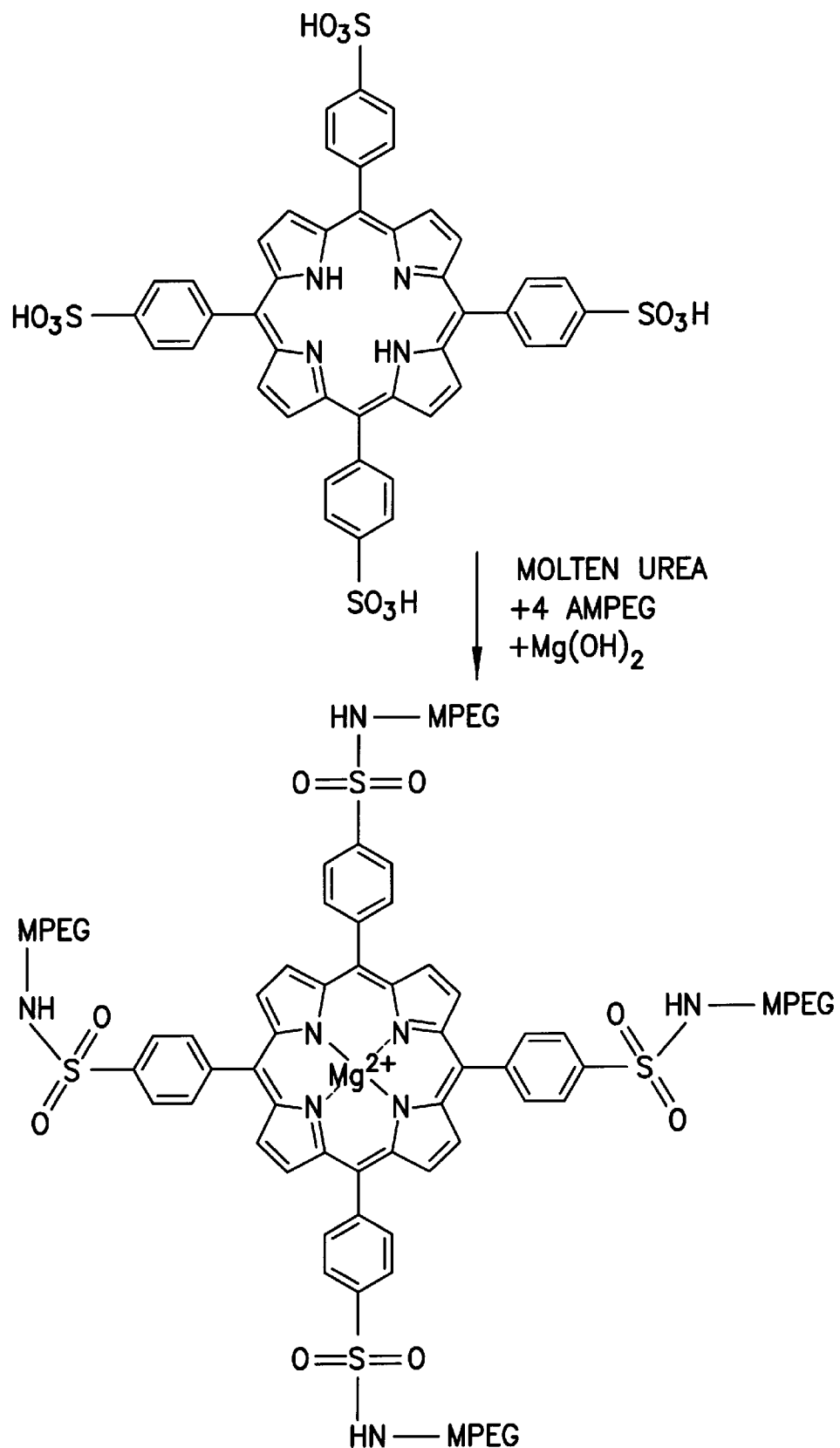
FIG. 6: shows the simultaneous metalation and acid amide formation.

The reaction is shown in FIG. 6.

About 40 mg of TSPP (tetra-(4-sulfophenyl)porphin, molecular weight ~934) (0.043 mM) were charged together with about 3.5 g of urea, 70 mg of $Mg(OH)_2$ (1.2 mM) and 1.2 g of AMPEG 0.24 mM) into a 15 m vial having a bead closure, tightly sealed with a silicone rubber plug and an aluminum cap and heated in a steam autoclave to 155° C. for 15 minutes.

After cooling down to about 105° C., the autoclave was aerated, the reaction vessel was removed and the mostly solidified molten urea was dissolved in 10 ml of distilled water. The clear, dichroic solution was transferred into an ultrafiltration cell for the purpose of purification and separation of undesired accompanying substances and washed 4 to 5 times on an ultrafilter (Amicon, YM 10) (depletion factor $>2\times10^5$). The product can be lyophilized and be dissolved in water having any pH or in organic solvents (DMF, DMAA, DMSO, DMPH(U)).

What is claimed is:

1. A process for preparing an acid amide, comprising reacting an acid with an aliphatic amine in molten urea.

2. The process according to claim 1, wherein the acid is selected from the group consisting of: carboxylic acid, sulfonic acid and phosphonic acid.

3. The process according to claims 1 wherein the acid is selected from the group consisting of: diethylenetriamine pentaacetic acid, diethylenetriamine pentamethylene phosphonic acid, an acid group-containing porphyrine, an acid group-containing phthalocyanine, an acid group-containing naphthalocyanine, an acid group-containing chlorin, an acid group-containing bacteriochlorine, an acid group-containing chlorophyll, an acid group-containing bacteriochlorophyll and derivatives thereof.

4. The process according to claim 1 wherein the aliphatic amine is a primary or secondary aliphatic amine.

5. The process according to claim 4, wherein the aliphatic amine is selected from the group consisting of: tris, glucamine, glucosamine and aminopolyether.

6. The process according to claim 1 wherein the reaction temperature is from about 120 to about 170° C.

7. The process according to claim 1 wherein the reaction is carried out for 1 minute to 12 hours.

8. The process according to claim 1 wherein the acid is also reacted with a metal ion in the molten urea.

9. A process for metalating a compound which can be bonded to a metal ion, comprising reacting the compound with a metal ion in molten urea.

10. The process according to claim 9, wherein the compound which can be bonded to a metal ion is an acid.

11. The process according to claim 8 wherein the metal ion is an ion of a metal selected from the group consisting of: Al, Mg, Zn, Cu, Co, Fe, Ni, Pt, Pd, Gd, Ga and In.

12. The process according to claim 8 wherein the reaction temperature is from about 120 to about 170° C.

13. The process according to claim 8 wherein the reaction is carried out for 1 minute to 12 hours.

14. A process for preparing an acid amide comprising reacting an acid with an aliphatic amine in molten urea, wherein:

(a) the acid is selected from the group consisting of carboxylic, sulfonic and phosphonic acid and wherein the aliphatic amine acid is selected from the group consisting of diethylenetriamine pentaacetic acid, diethylenetriamine pentamethylene phosphonic acid, an acid group-containing porphyrine, an acid group-containing phthalocyanine, an acid group-containing naphthalocyanine, an acid group-containing chlorin, an acid group-containing bacteriochlorine, an acid group-containing chlorophyll, an acid group-containing bacteriochlorophyll and derivatives thereof; and (b) wherein the reaction temperature is from about 120 to about 170° C.

15. The process of claim 1 wherein the aliphatic amine is supplied in excess of acid groups of the acid to which the amine will bond.

16. The process of claim 1 wherein the reaction is carried out for about 10 to about 20 minutes.

17. The process according to claim 9 wherein the compound which can be bonded to a metal ion is selected from the group consisting of: carboxylic acid, sulfonic acid and phosphonic acid.

18. The process according to claim 9 wherein the compound which can be bonded to a metal ion is selected from the group consisting of diethylenetriamine pentaacetic acid, diethylenetriamine pentamethylene phosphonic acid, porphyrines, phthalocyanines, naphthalocyanines, chlorins, bacteriochlorins, chlorophylls, bacteriochlorophylls and derivatives thereof.

19. A method for preparing a metallized acid amide comprising one or more steps selected from the group consisting of:

(a) reacting an acid with an aliphatic amine in molten urea to provide an acid amide;

(b) reacting an acid amide with a metal ion in molten urea; and (c) reacting an acid with a metal ion in molten urea.

20. The method according to claim 19 wherein the steps comprise (a) then (b).

21. A method according to claim 19 wherein the steps comprise (a) and (c) simultaneously.

22. The method of claim 1 wherein the acid is $Gd^{3+}$-containing diethylenetriamine pentaacetic acid, and the amine is amino-Ω-methoxy-polyethylene glycol.

23. The method of claim 1 wherein the acid is $Gd^{3+}$-containing diethylenetriamine pentamethylene phosphonic acid, and the amine is amino-Ω-methoxy-polyethylene glycol.

24. The method of claim 1 wherein the acid is tetra-(4-sulfophenyl)porphin, and the amine is amino-Ω-methoxy-polyethylene glycol.

25. The method of claim 1 wherein the acid is tetra-sulfophthalocyanine, and the amine is amino-Ωmethoxy-polyethylene glycol.

26. The method of claim 9 wherein the acid is tetra-(4-carboxyphenyl)porphin, the amine is amino-Ω-methoxy-polyethylene glycol and the metal is $Mg^{++}$.

27. A method for simultaneous metallization and acid amide formation comprising reacting an acid, an aliphatic amine, and a metal ion in molten urea.

28. The method according to claim 27 wherein the acid is tetra-(4-sulfophenyl)porphin, the amine is amino-Ω-methoxy-polyethylene glycol and the metal is $Mg^{++}$.

* * * * *